US012364778B1

(12) United States Patent
Dooley (10) Patent No.: US 12,364,778 B1
(45) Date of Patent: Jul. 22, 2025

(54) PORTABLE DISINFECTION APPARATUS, AND SYSTEM AND METHOD FOR TRACKING DISINFECTION

(71) Applicant: Kreative Zeno Systems, Inc., San Antonio, TX (US)

(72) Inventor: Thomas W. Dooley, Mico, TX (US)

(73) Assignee: Kreative Zeno Systems, Inc.

( * ) Notice: Subject to any disclaimer, the term of this patent is extended or adjusted under 35 U.S.C. 154(b) by 0 days.

(21) Appl. No.: 18/462,134

(22) Filed: Sep. 6, 2023

(51) Int. Cl.
*A61L 2/10* (2006.01)

(52) U.S. Cl.
CPC ............. *A61L 2/10* (2013.01); *A61L 2202/11* (2013.01); *A61L 2202/14* (2013.01); *A61L 2202/16* (2013.01)

(58) Field of Classification Search
CPC .... A61L 2/10; A61L 2202/11; A61L 2202/14; A61L 2202/16
See application file for complete search history.

(56) References Cited

U.S. PATENT DOCUMENTS

| | | | |
|---|---|---|---|
| 4,167,669 A | | 9/1979 | Panico |
| 5,968,455 A | * | 10/1999 | Brickley .................. A61L 9/20 362/267 |
| 6,030,578 A | * | 2/2000 | McDonald ................ A61L 2/08 422/186 |
| 8,907,258 B2 | | 12/2014 | Schroder et al. |
| 9,599,397 B2 | | 3/2017 | Jackson |
| 10,004,822 B2 | | 6/2018 | Stibich et al. |
| 10,410,853 B2 | | 9/2019 | Stibich et al. |
| 10,634,555 B2 | | 4/2020 | Wilk et al. |
| 10,842,894 B1 | | 11/2020 | Provost et al. |
| 10,865,959 B2 | | 12/2020 | Wilk et al. |
| 10,894,106 B1 | * | 1/2021 | Lopez ....................... A61L 2/20 |
| 10,959,441 B2 | | 3/2021 | Hathaway et al. |

(Continued)

FOREIGN PATENT DOCUMENTS

| | | | | |
|---|---|---|---|---|
| CA | 3084734 A1 | * | 12/2021 | ............... A61L 2/10 |
| WO | WO-2021133815 A2 | * | 7/2021 | ............... A61L 2/10 |

OTHER PUBLICATIONS

Ronit Mandal et al., Applications of Pulsed Light Decontamination Technology in Food Processing: An Overview, 10 Applied Sciences 3606 (May 22, 2020).

(Continued)

*Primary Examiner* — Regina M Yoo
(74) *Attorney, Agent, or Firm* — Edward B. Marvin; Jackson Walker LLP (57) ABSTRACT

The present disclosure concerns a portable disinfection apparatus, as well as a system and method for tracking disinfection. The apparatus generally comprises an enclosure having an ultraviolet (UV) light source mounted on a rolling mechanism. UV light from the UV light source travels toward a ground surface and disinfects one or more areas or features of the ground surface. The apparatus may also have a scanner or machine reader that reads data encoded on an object each time disinfection occurs. The disinfection events can be logged to create a disinfection event log, thereby tracking the frequency of disinfection events. Additionally, the encoded object may be configured as an image that is placed relative to the floor drain or other to be disinfected such that a user can confirm the apparatus is in the proper location to disinfect the item to be disinfected.

14 Claims, 5 Drawing Sheets

(56) References Cited

U.S. PATENT DOCUMENTS

| | | | | |
|---|---|---|---|---|
| 2005/0022330 | A1* | 2/2005 | Park | G05D 1/0246 15/319 |
| 2005/0022844 | A1* | 2/2005 | Field | E01H 1/042 134/6 |
| 2010/0223843 | A1 | 9/2010 | Williams | |
| 2010/0314553 | A1* | 12/2010 | Yerby | A61L 2/10 250/455.11 |
| 2011/0274582 | A1* | 11/2011 | Davis | A61L 2/10 280/78 |
| 2012/0168647 | A1* | 7/2012 | Davis | A61L 2/10 250/492.1 |
| 2012/0223216 | A1* | 9/2012 | Flaherty | G05D 1/0242 901/1 |
| 2014/0042342 | A1 | 2/2014 | Karim et al. | |
| 2016/0213798 | A1* | 7/2016 | Paver, Jr. | A61L 2/22 |
| 2020/0254122 | A1* | 8/2020 | Starkweather | A61L 2/10 |
| 2021/0137328 | A1* | 5/2021 | Tien | A47L 11/4061 |
| 2021/0338864 | A1* | 11/2021 | Urban | G07F 17/3216 |
| 2021/0369015 | A1* | 12/2021 | Nevitt | A61L 2/10 |
| 2021/0402021 | A1* | 12/2021 | Nevitt | A61L 2/10 |
| 2022/0066456 | A1* | 3/2022 | Ebrahimi Afrouzi | A47L 9/2873 |
| 2022/0370671 | A1* | 11/2022 | Starkweather | G16H 40/20 |
| 2023/0293745 | A1* | 9/2023 | Shigoku | A61L 9/20 422/24 |

OTHER PUBLICATIONS

Zuzana Bohrerova et al., Comparative disinfection efficiency of pulsed and continuous-wave UV irradiation technologies, 42 Water Research 2975 (2008).

XENON Corporation, Brochure titled "The Power of Pulsed Light to Aid Decontamination of Food Conveyors" (2019).

Stephen A. Craik et al., Inactivation of Cryptosporidium Parvum Oocysts Using Medium- and Low-Pressure Ultraviolet Radiation, 35(6) Water Research 1387 (2001).

Eva Hierro et al., Efficacy of pulsed light for shelf-life extension and inactivation of Listeria monocytogenes on ready-to-eat cooked meat products, 12 Innovative Food Sci. & Emerging Techs. 275 (2011).

Ying Guo, Effects of Pulsed Light on Microbial Decontamination of Dry Food Powder and Food Processing Aids (2013) (M.Sc. thesis, University of Florida).

XENON Corporation, Brochure titled "Improving the Safety and Quality of Food with Pulsed Light by XENON" (2020).

XENON Corporation, Brochure titled "10 Reasons Why Pulsed Light Is Selected as an Antimicrobial Process" (2015).

Ali Demirci, Poster titled "Decontamination of Foods by Pulsed Ultraviolet Light," place of initial publication unknown (published prior to Sep. 6, 2023).

Stephen R. Wilk, XENON Corporation, Brochure titled "Pulsed Ultraviolet Light as an Element of Hurdle Technology for Sanitizing Conveyor Belts" (published prior to Sep. 6, 2023).

XENON Corporation, Brochure titled "Pulsed UV Light—An Effective Technology for Clean Rooms" (2015).

XENON Corporation, Brochure titled "Applications of Pulsed Light for Sterilization" (2015).

XENON Corporation, Brochure titled "The Power of Pulsed Light to Control Pathogen Contamination" (2016).

XENON Corporation, Brochure titled "NENON RC-800: Modular UV Curing System" (2014).

Business Wire, Xenex Announces DEACTIVATE Handheld Disinfection Device; Proven to Destroy SARS-CoV-2 on Surfaces in 30 Seconds (Feb. 10, 2021).

AcuityBrands, Webpage for "Pulsed Xenon UV Disinfection Technology" (published prior to Sep. 6, 2023).

Amazon.com webpage, search for "hand truck nose plate" (published prior to Sep. 6, 2023).

McMaster-Carr webpage, search for "ball wheels" (published prior to Sep. 6, 2023).

Global Industrial webpage, product page for "Cast Aluminum 18"×7½" Nose Plate for Magliner(R) Hand Trucks" (published prior to Sep. 6, 2023).

XENON Corporation, Product Sheet for "XENON CIXL" (2016).

U.S. Dept. of Health & Human Svcs., "Control of Listeria monocytogenes in Ready-To-Eat Foods: Guidance for Industry" (2017).

Hevi-Haull, webpage article titled "Hand-Truck vs Dolly: What's the Difference" (published prior to Sep. 6, 2023).

Caster Central, webpage article titled "Hand Truck vs. Dolly: Differences and Choosing the Right Caster Wheels for Each" (published prior to Sep. 6, 2023).

The WEBstaurant Store, LLC, webpage article titled "Hand Trucks vs Dollies" (published prior to Sep. 6, 2023).

Douglas Equipment, webpage article titled "What Is the Difference Between a Dolly, Hand Truck, and a Folding Hand Truck?" (published prior to Sep. 6, 2023).

USDA, "Inspection Methods Refresher Course Student Handout" (published prior to Sep. 6, 2023).

USDA—FSIS Directive, "Listeria Rule Verification Activities" (published prior to Sep. 6, 2023).

* cited by examiner

PORTABLE DISINFECTION APPARATUS, AND SYSTEM AND METHOD FOR TRACKING DISINFECTION

CROSS-REFERENCES TO RELATED APPLICATIONS

None

BACKGROUND

1. Field of the Invention

The present disclosure relates generally to ultraviolet light (UV) disinfection systems. More specifically the disclosure relates to a portable disinfection apparatus, as well as a system and methods for tracking disinfection of items.

2. Description of the Related Art

The ability for ultraviolet ("UV") light to kill harmful pathogens is well-known in the art and many different UV light disinfection systems have developed over the years. These systems use a variety of technologies to harness UV light from the sun and/or to generate UV light for disinfection. As an example of the latter, mercury vapor lamps, xenon flash lamps, or other UV lamps can provide suitable UV light radiation to kill pathogens such as bacteria, viruses, molds, and other harmful microorganisms present on the surface of almost any workpiece.

Some UV disinfection systems are directed to disinfecting workpieces while traveling on a conveyor belt. For example, U.S. Pat. No. 10,959,441, assigned to Xenon Corporation (the "Xenon Patent"), discloses using UV light radiation in the treatment of food products such as blueberries. As another example, U.S. Pat. No. 10,842,894, assigned to Steribin, LLC (the "Steribin Patent"), uses UV light radiation to disinfect airport security bins. In both instances, the UV lamp disinfects the workpieces as they ride on the belt past UV light rays emitted from the lamp. These rays may be constantly emitted from the lamp such as in a mercury vapor system or may come in flashes or pulses such as in a xenon flash lamp system.

Disinfection systems such as those discussed above are statically positioned. In this regard, the UV lamp is placed in a position that does not move relative to the item to be disinfected and problems concerning disinfection efficacy arise. Recognizing these problems, Applicant devised a solution for a disinfection system that includes a displaceable UV lamp to achieve optimal disinfection efficacy for items traveling on a conveyor belt, as reflected in U.S. patent application Ser. No. 17/854,845, filed Jun. 30, 2022, which is hereby incorporated by reference in its entirety ("Applicant's Prior Application").

However, the disinfection systems discussed above, and the system disclosed in Applicant's Prior Application, are all directed to disinfecting items on a conveyor belt, and the systems as a whole stay relatively static while the items to be disinfected are conveyed under their disinfecting UV lamps. These systems are not designed to be transported from location to location to disinfect items. They are not portable.

There is a need for portable disinfection systems. For example, in the food industry, food processing plants must continually clean their equipment and many food processing plants are washdown environments. As the equipment is washed down, water potentially containing pathogens in the form of bacteria or other microorganisms (e.g., *salmonella, campylobacter, E. coli, listeria*, etc.) is directed to floor drains.

However, the floor drains themselves can harbor harmful bacteria and other microorganisms. For example, listeriosis outbreaks have been traced to particles carrying *listeria* emitted from floor drains. It is also generally known that high-pressure sprays while cleaning certain types of drains can cause *listeria* to become airborne in production facilities. Thus, there exists a need for drain disinfection measures that prevent pathogens from becoming airborne in production facilities. It is an object of the present invention to address such a need.

Government regulatory agencies recognize the concerns related to unsanitary floor drains and the potential harmful effect to food production. Agencies such as the Food and Drug Administration ("FDA") and the United States Department of Agriculture ("USDA") have developed regulations requiring food production facilities to implement standard operating procedures ("SOPs") concerning the sanitation measures the facility will employ to prevent contamination or adulteration of the food product. The FDA and USDA also require production facilities to follow the SOPs the facilities implement and keep daily records demonstrating the facilities' compliance with their SOPs. Thus, there exists a need for disinfection measures to be implemented and tracked with records to demonstrate compliance with SOPs. It is an object of the present invention to address such a need.

Commonly, food production facilities use cleaning agents, acid, or other hazardous chemicals to sanitize drains. However, use of these chemicals creates a risk of inadvertent harmful exposure to the personnel administering the chemicals or to the food products if not adequately flushed, as well as other risks. Further, disinfection chemicals may pollute the environment and present disposal concerns. Thus, there exists a need for disinfection methods that reduce the risks associated with chemical usage to sanitize or disinfect parts of food production facilities. It is an object of the present invention to address such a need.

BRIEF SUMMARY

Disclosed herein is an apparatus, system, and method for disinfecting floor drains and other ground surface areas, as well as other items on a ground surface, using a portable disinfection apparatus. In some embodiments the apparatus comprises an ultraviolet (UV) light source mounted on at least one rolling mechanism. The UV light source is housed within an enclosure and emits disinfecting UV light onto a ground surface containing a floor drain. The rolling mechanism allows the UV light source to be easily transported from one location to another within a facility, thus enabling multiple floor drains to be efficiently sanitized.

Preferably, the enclosure housing the UV light source is mounted on a plate and the plate is mounted on the rolling mechanism. In some embodiments, the plate rests on and is connected to a nose plate on a hand truck. The nose plate preferably has a central opening though which UV light from the UV light source can travel. However, in alternative embodiments the enclosure may be mounted directly on the hand truck or other rolling mechanism.

When present, the plate has a first opening through which UV light emitted from the UV light source travels to reach the ground surface. In some embodiments, the plate may have a second opening through which an air stream containing an air/ozone mixture is directed. The air stream forces ozone generated by the UV light source into the drain, which further provides a sanitizing effect given ozone's propensity to kill aerobic organisms such as molds or other aerobic organisms that may be present.

In some embodiments, a skirt extends from the plate to the ground surface. The skirt helps contain ozone generated by the UV light source within a chamber formed by the ground surface, the plate, and the skirt, thereby helping prevent potentially harmful ozone exposure.

In some embodiments, the portable disinfection apparatus has a scanner or machine reader to detect encoded data from a label or tag positioned near the item or area to be disinfected. The scanner may emit visible light to scan an image (e.g., a barcode, QR code, or other automatic data capture images) or use other automatic identification and data capture techniques (e.g., radio frequency identification (RFID), magnetic stripes, etc.). The scanner helps track disinfection events associated with the drain or other item to be disinfected, thereby facilitating compliance with sanitation SOPs or other disinfection protocols.

In some embodiments, the scanner may be used to properly position the portable disinfection apparatus for optimal disinfection. For example, optical scanners that emit visible light can be used to properly align the UV light source over the drain that requires disinfection. In such an embodiment, the label or tag read by the optical scanner contains an image and the visible light from the optical scanner is aligned with the image. The image is positioned in a location to ensure proper alignment of the UV light source, depending on the specific location of the UV light footprint relative to the visible light emitted from the optical scanner.

In further embodiments, the encoded data read by the scanner can be transmitted to a computing device with a receiver and the computing device logs the disinfection events. In such embodiments, for example, the portable disinfection apparatus may be programmed such that the scanner scans the label or tag when the UV light source is activated to disinfect the desired disinfection item or area. A time and date stamp is captured each time disinfection occurs and the data is transmitted to the receiver to report a disinfection event. The computing device then logs the disinfection events into an event log, thus allowing disinfection events to be tracked and further facilitating compliance with sanitation SOPs or other disinfection protocols.

In even further embodiments, the rolling mechanism may be part of an autonomous robot or vehicle. In such embodiments, the autonomous robot or vehicle may be placed in a learning mode to learn the location(s) of the drain(s) or other items to be disinfected. Once the location(s) is/are learned, the autonomous robot or vehicle can then be switched to automatic mode to disinfect the drain(s) or other items to be disinfected. Such embodiments may incorporate use of the scanner to properly position the portable disinfection apparatus for optimal disinfection.

DETAILED DESCRIPTION

Figure 1:
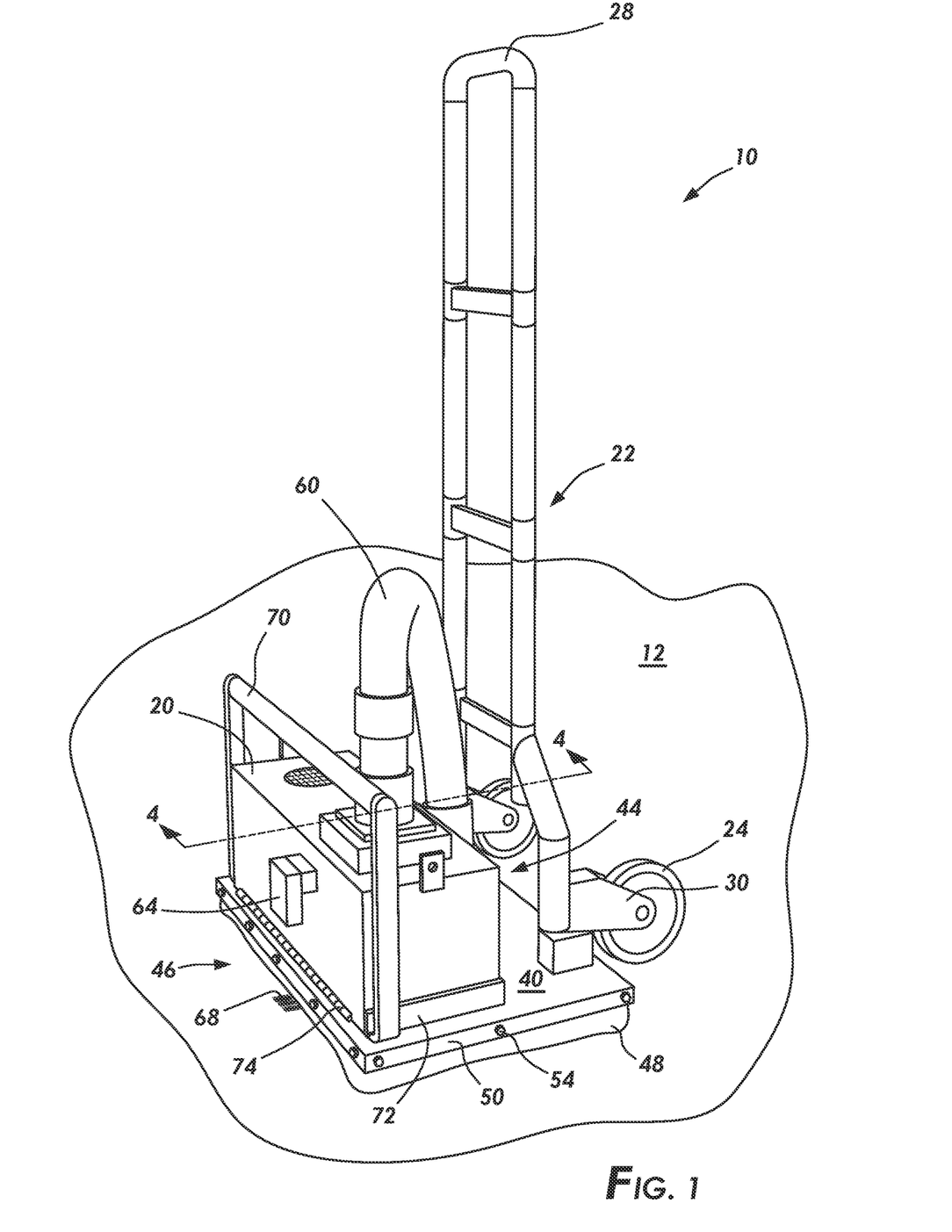
FIG. 1 shows a side perspective view of an embodiment of the present disclosure taken from the right side of the embodiment.
Figure 2:
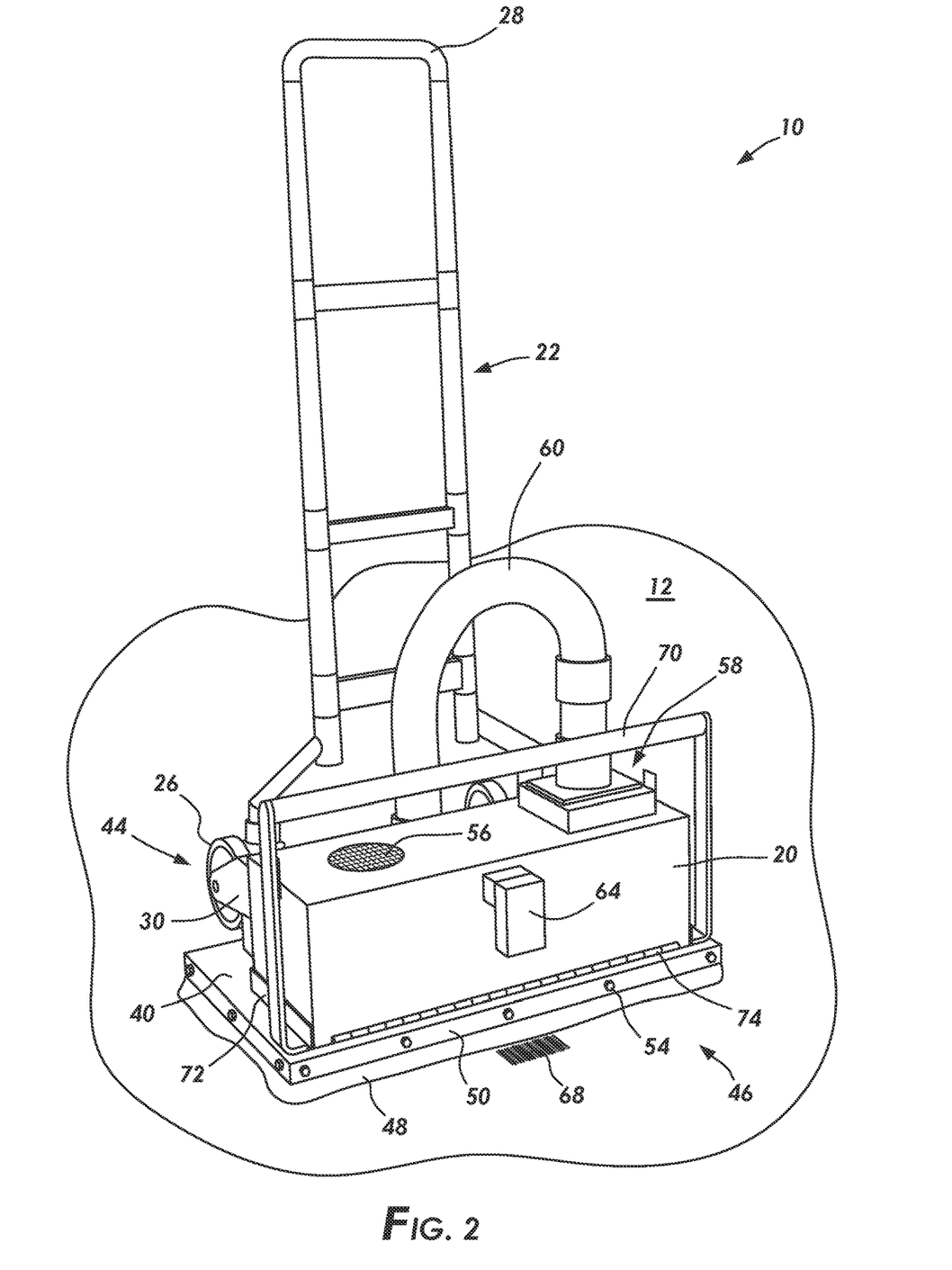
FIG. 2 shows a front perspective view of the embodiment in FIG. 1.

FIGS. 1 and 2 show an embodiment 10 of the present invention placed on a ground surface 12. The embodiment 10 generally comprises an enclosure 20 that houses at least one ultraviolet (UV) light source. The enclosure 20 is mounted on at least one rolling mechanism.

The illustrated rolling mechanism is a wheeled device in the form of a hand truck 22. The hand truck 22 has a first wheel 24 and a second wheel 26 attached to a handle 28 by a fork 30. A nose plate (not shown) extends from the base of a handle 28 and typically rests on the ground surface 12, though in the present embodiment measures are implemented to separate the nose plate from the ground surface 12, as discussed below.

It should here be noted that the term "rolling mechanism" is meant in its broadest form and encompasses anything that is able to roll on the ground surface 12 such as, for example and without limitation, wheel casters, ball casters, rollers, wheels within a continuous track (i.e., tracked vehicle propulsion), dollies, wagons, and carts.

With the illustrated rolling mechanism, the handle 28 of the hand truck 22 is telescopic. As such, it can be shortened from its extended form shown in FIGS. 1 and 2 to a collapsed form (not shown) for storage and/or transport. In alternative embodiments, however, the handle 28 may have a fixed length that does not change, or the handle 28 may not be present depending on the form of the rolling mechanism.

The enclosure 20 rests on a plate 40, while the plate 40 rests on the nose plate (not shown) of the hand truck 22. The plate 40 has a perimeter that includes a rear end 44 and a front end 46. The rear end 44 is near the first and second wheels 24, 26 of the hand truck 22, while the front end 46 is opposite the rear end 44.

A skirt 48 extends from the plate 40 to the ground surface 12. The skirt 48 preferably extends from the plate 40 around the entire perimeter of the plate 40. The skirt 48 helps prevent ozone generated by the UV light source from escaping the volume under the plate 40. In this regard, the skirt 48, the plate 40, and the ground surface 12 form a chamber under the plate 40 that contains ozone generated by the UV light source. Accordingly, the ozone, which can be harmful to humans, is prevented from entering the atmosphere where a user of the apparatus is located, and one can safely use the apparatus. The skirt 48 may be made from any material that safely contains the ozone but is preferably durable enough to withstand the rigors of use. It has been found that silicone rubber (e.g., FDA/USDA approved rubber per 21 C.F.R. § 177.2600) is suitable for such a purpose, though other materials would be suitable.

The skirt 48 may be mounted on the plate 40 in a variety of ways. In the embodiment 10, at least one sidewall 50 extends from the perimeter of the plate 40 and the skirt is placed on along the inner surface of the sidewall. The sidewall 50 may be a single continuous wall as shown or may have one or more breaks around the perimeter. One or more bolts 54 extend through the sidewall 50 and through the skirt 48 to hold the skirt 48 in place. Preferably, a strip of rigid material (not shown) extends along the interior of the skirt 48 and receives the one of more bolts 54. Such a design sandwiches the skirt 48 between the sidewall 50 and the strip of rigid material, thereby adding durability. However, large washers or other rigid support mechanisms may achieve the same purpose. Additionally, the skirt 48 may be positioned against the exterior of the sidewall 50, with the strip of rigid material extending along the outer surface of the skirt 48.

The enclosure 20 has an air inlet 56 and an exhaust outlet 58 for cooling the UV light source housed therein. A fan (not shown) within the enclosure 20 pulls atmospheric air into the inlet 56. The air then moves across the UV light source to cool the UV light source (not shown) and exits the exhaust outlet 58. Ozone is generated by the UV light source also exits from the exhaust outlet 58, thus creating an air/ozone mixture. The exhaust outlet 58 is connected to a hose 60, and the hose 60 conducts an air stream comprising an ozone and air mixture, as further discussed below.

The embodiment 10 also comprises a scanner 64 mounted on the exterior of the enclosure 20, though it could be mounted in other locations. The scanner 64 scans an encoded object to record a disinfection event using automatic identification and data capture techniques. More specifically, each time the UV light source is activated to generate UV disinfecting light, the scanner 64 reads the encoded object to record a disinfection event, and a time and date stamp is associated with the disinfection event. As such, the scanner 64 and the encoded object work as a system to track each time a disinfection event occurs.

The scanner 64 may be any type of machine reader for reading data from the encoded object. For example, an optical scanner that reads encoded barcodes or QR codes, a radio frequency identification (RFID) reader that reads encoded information from a transmitter, and a magnetic stripe reader that reads magnetic stripes, as well as others, may suffice.

Preferably, the scanner 64 and encoded object are used as a system to correctly position the portable disinfection apparatus for disinfection. In this regard, the encoded object may be placed in a location that confirms the portable disinfection apparatus is in the correct position to disinfect a drain or other item to be disinfected.

For example, in the illustrated embodiment 10, the scanner 64 is an optical scanner that emits visible light and the encoded object is a barcode 68 placed on the ground surface 12. The barcode 68 is located a predetermined distance from the drain or other area on the ground surface 12 to be disinfected. Such location depends on the specific design of the portable disinfection apparatus.

For example, if the center of the UV light footprint is twelve inches away from the center of the visible light from the scanner 64, the barcode 68 is located twelve inches from the center of the drain or other area on the ground surface 12 to be disinfected so that the center of the drain or other item to be disinfected aligns with the center of the UV light footprint. Accordingly, the greatest intensity of the UV light emitted from the UV light source will encounter the drain or other area to be disinfected when the visible light from the scanner 64 is aligned with the barcode 68. The proper placement of the barcode or other images could be specified through use of a template depending on the specific application.

A secondary handle 70 is also shown in the embodiment 10. The secondary handle 70 facilitates transport of the embodiment 10 such as, for example, when traversing stairs or loading/unloading the portable disinfection apparatus from a vehicle. As shown, the secondary handle 70 is attached to the plate 40 at locations adjacent the front end 46 and it extends over the plate 40 and the enclosure 20.

The enclosure 20 in the illustrated embodiment 10 has a lid 72 with a hinge 74. The hinge 74 allows the enclosure 20 to be opened for replacement of the UV light source bulb or other maintenance within the enclosure 20. Such design is present in the Compact Integrated Xenon Lamp ("CIXL") offered by the Xenon Corporation, which has been found to suitably serve as the UV light source. Advantageously, the CIXL offers an integrated power supply and cooling technology within the enclosure 20 which can be used in the present invention.

Figure 3:
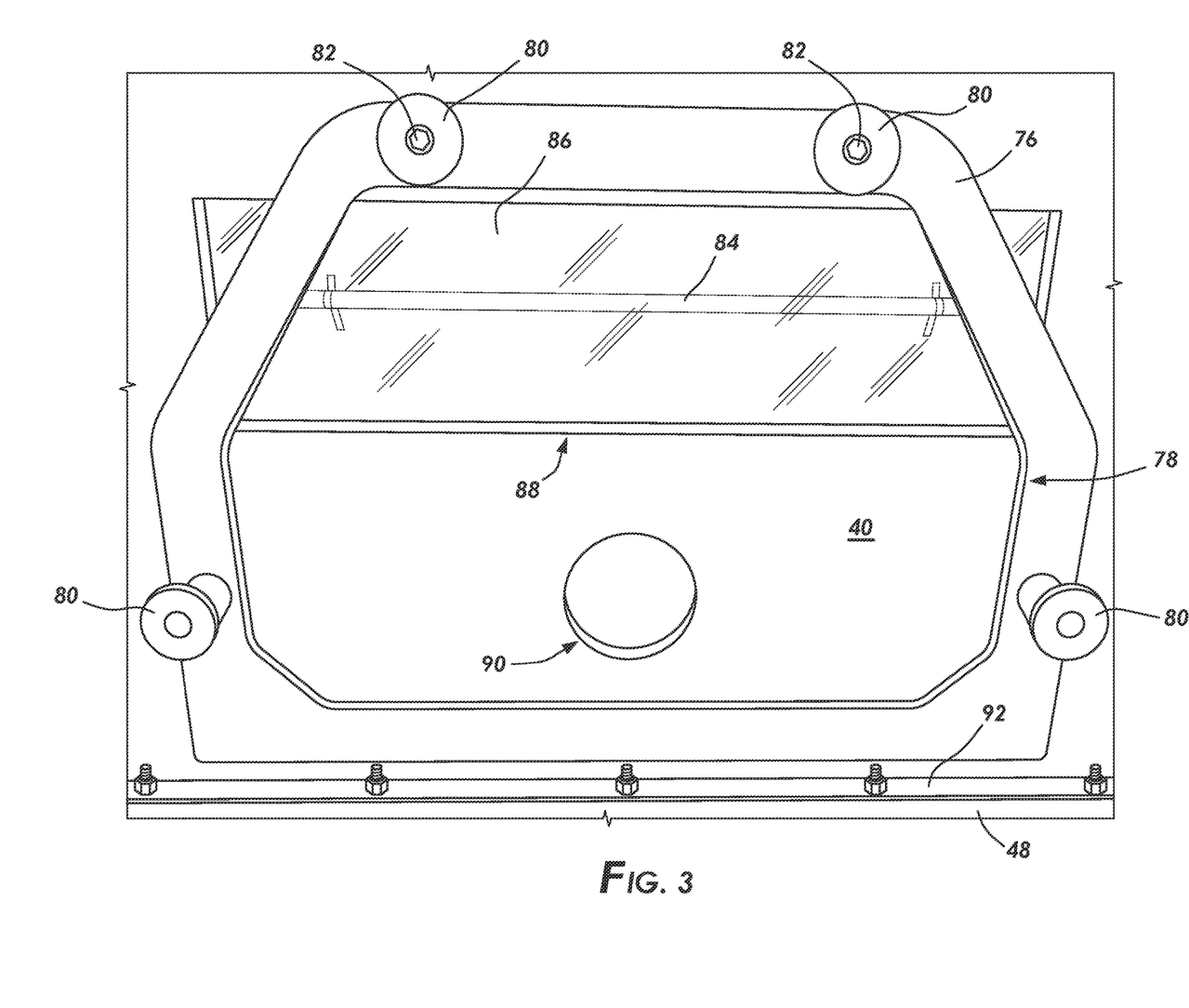
FIG. 3 shows a partial bottom perspective view of the embodiment in FIG. 1.

FIG. 3 shows a bottom view of the embodiment 10, with the nose plate 76 of hand truck in the foreground. The nose plate 76 has a central opening 78 through which elements can be seen, as discussed below. Additionally, one or more spacers 80 are attached to the nose plate 76 with bolts 82 that extend through the nose plate 76, through the plate 40, and into the enclosure 20. The spacers 80 prevent the nose plate 76 from resting directly on the ground surface (not shown) and prevent the UV light source from getting too close to the item to be disinfected. It has been found that spacers 80 which are one inch (1") long suffice for this purpose, however, the spacers 80 may be longer or shorter depending on the application.

The bulb 84 of the UV light source is also shown behind protective glass 86. The glass 86 is preferably quartz and acts as a lens because UV light emitted from the bulb 84 travels through the glass 86 during operation. In this regard, the bulb 84 is positioned within a reflector (not shown) that helps ensure all the UV light emitted from the bulb 84 proceeds toward the glass 86. The bulb 84 and the glass 86 are positioned over a first opening 88 disposed in the plate 40. As such, UV light emitted from the bulb 84 first travels through the glass 86, then through the first opening 88 in the plate 40, then through the central opening 78 in the nose plate 76, and finally to the ground surface (not shown).

Additionally, a second opening 90 is disposed in the plate 40. The second opening 90 is where the air/zone mixture exits from the hose (not shown). The exiting air forces the ozone generated by UV light source down the drain as further discussed below. Additionally, the strip of rigid material 92 can be seen along a portion of the skirt 48 that extends along the rear end of the plate 40.

Figure 4:
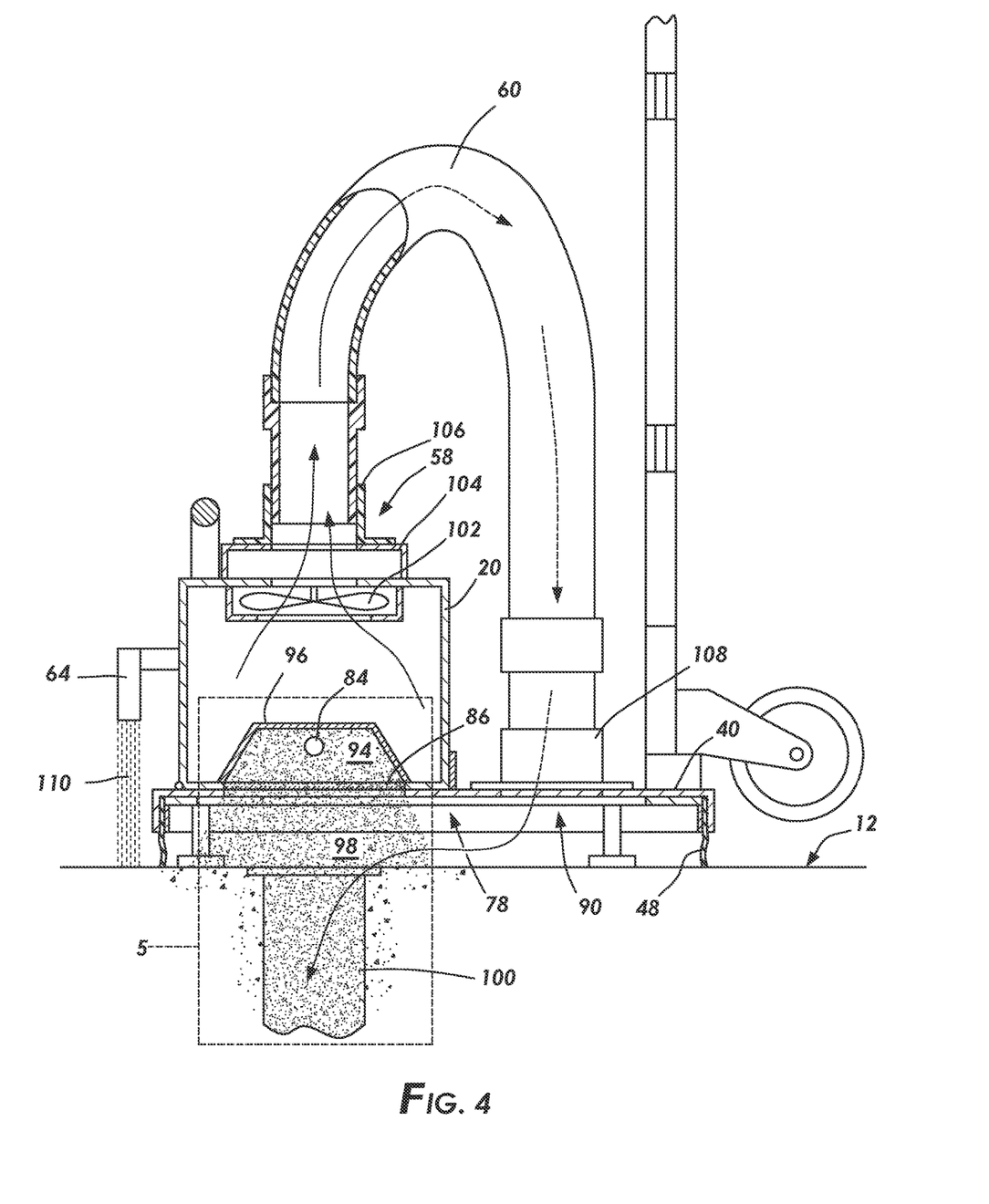
FIG. 4 is a partial cross section view of the embodiment taken along section line 4-4 in FIG. 1 with arrows to illustrate air movement.
Figure 5:
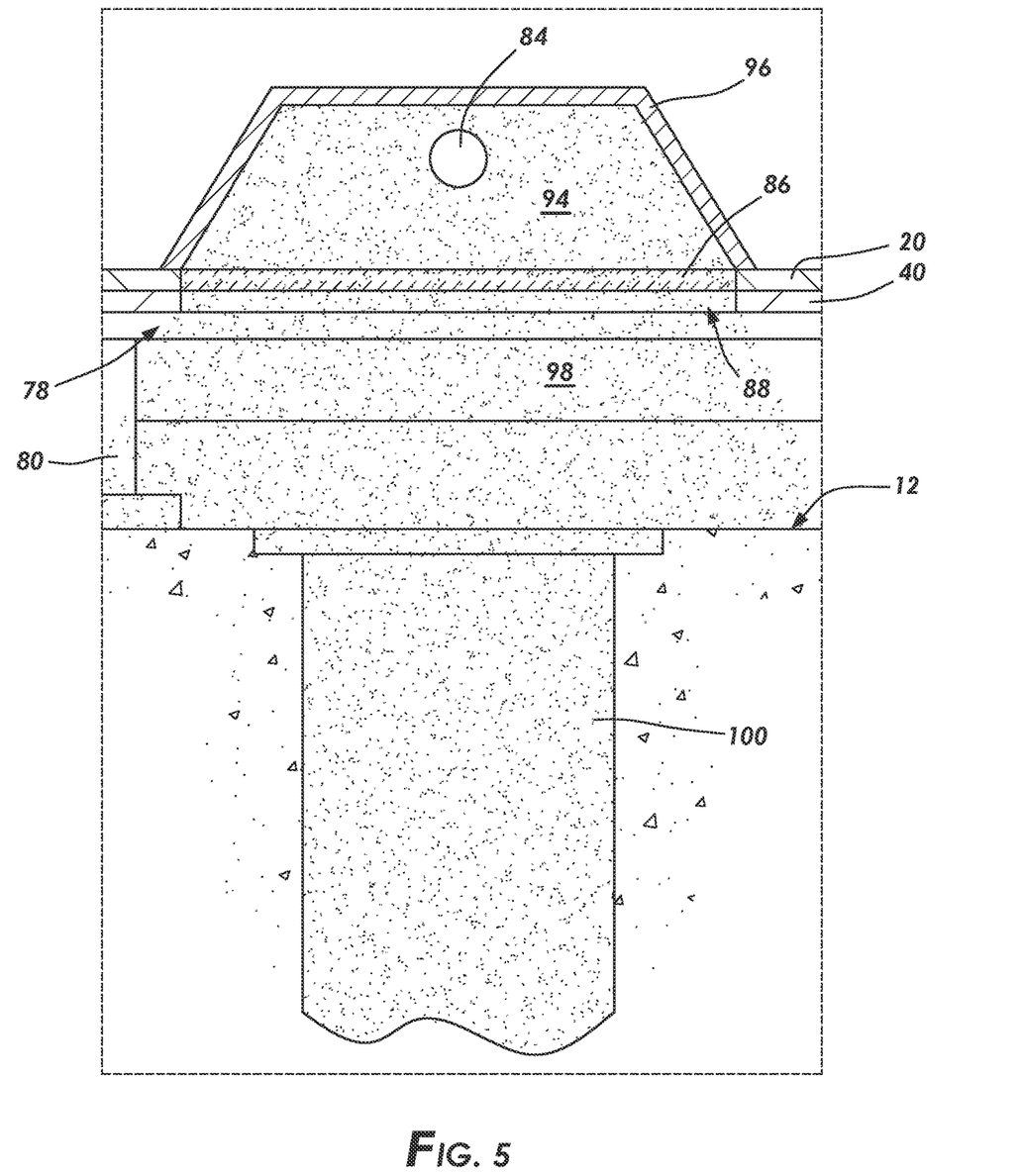
FIG. 5 is a close-up, cutaway view of the embodiment from FIG. 4.

FIGS. 4 and 5 demonstrate portable disinfection apparatus in operation. As shown, UV light 94 emitted from the bulb 84 is directed to the glass 86, in part, by the reflector 96. UV light 98 exits the glass 86 and travels through the first opening 88 of the plate 40 and through the central opening 78 of the nose plate 76 toward the ground surface 12. The UV light 98 encounters a drain 100 in the ground surface 12 and travels into the drain 100 to disinfect it.

Meanwhile, a fan 102 within the enclosure 20 pulls the air/ozone mixture from within the enclosure 20 into the exhaust outlet 58 into the hose 60, as shown in FIG. 4. The fan 102 directs the air/ozone mixture past a riser 104 and into a first hose connector 106 that connects the hose 60 to the riser 104. The air/ozone mixture then flows into the hose 60 and through the hose 60 to a second hose connector 108 that connects to the hose 60 to the second opening 90 in the plate 40. The air/ozone mixture then exits the second opening 90 into the chamber created by the skirt 48, the plate 40, and the ground surface 12, and the fan 102 pushes the ozone generated by the UV light source into the drain 100. The ozone is heavier than air, and this heavy gas property, along with the force from the fan 102, helps direct the ozone into the drain 100.

Additionally, the scanner 64 emits visible light 110 to scan the barcode (not shown), which (1) aligns the embodiment 10 in the proper position for the drain 100 to be disinfected and (2) records the disinfection event. The scanner 64 then transmits a record of the disinfection event to a receiver (not shown) that is part of a computing device. The record contains a time and date stamp or is assigned a time and date stamp by the computing device or the receiver. Preferably, the transmission is wireless, but alternative embodiments may include a wired transmission.

The receiver receives the disinfection event transmitted from the scanner 64 and the computing device stores the disinfection event. Over time, the scanner 64 transmits a plurality of disinfection events to the receiver and the computing device logs the plurality of disinfection events in a disinfection event log. The disinfection event log can then be consulted to determine whether the disinfection events over a specified time interval comply with the sanitation SOPs.

The present invention is described in terms of one or more specifically described embodiments which is/are presented for purposes of illustration and not of limitation. Those skilled in the art will recognize that alternative embodiments not specifically described herein can be used in carrying out the present invention. Other aspects and advantages of the present invention may be obtained from a study of this disclosure and the drawings, along with the appended claims.

I claim:

1. A portable disinfection apparatus comprising:
a plate having first opening and a second opening disposed therein, said plate being mounted on at least one rolling mechanism;
an enclosure mounted on the plate over the first opening, said enclosure having an exhaust outlet for emitting an air stream from said enclosure, said air stream being directed through the second opening;
an ultraviolet light source housed within the enclosure, said ultraviolet light source being positioned to emit ultraviolet light through the first opening; and
a hose extending between the exhaust outlet and the second opening.

2. The portable disinfection apparatus of claim 1 further comprising a skirt extending from the plate to a ground surface.

3. The portable disinfection apparatus of claim 1 wherein the plate has a perimeter with a front end and a rear end opposite said front end, and said portable disinfection apparatus further comprises a handle extending from a location on the plate adjacent the front end.

4. The portable disinfection apparatus of claim 3 wherein the handle extends over the plate and over the enclosure.

5. The portable disinfection apparatus of claim 1 further comprising a scanner that reads an encoded object to record a disinfection event.

6. The portable disinfection apparatus of claim 5 wherein the scanner is mounted on the enclosure.

7. The portable disinfection apparatus of claim 5 wherein the scanner is an optical scanner, and the encoded object is an image on a ground surface.

8. The portable apparatus of claim 1 wherein the at least one rolling mechanism comprises a hand truck with wheels.

9. A portable disinfection apparatus for a ground surface comprising:
a hand truck with a handle and a nose plate;
an enclosure on the hand truck in a position above the nose plate, said enclosure having an exhaust outlet for emitting air from the enclosure;
a plate between the enclosure and the nose plate, said plate having a first opening and a second opening disposed therein;
an ultraviolet light source housed within the enclosure; and
a hose extending between the exhaust outlet and the second opening;
wherein the ultraviolet light source emits ultraviolet light through the first opening onto an area of the ground surface to disinfect the area and the air is directed through the second opening.

10. The portable disinfection apparatus of claim 9 wherein the nose plate further comprises a central opening aligned with the first opening in the plate and the ultraviolet light is emitted through the central opening.

11. The portable disinfection apparatus of claim 9 further comprising a skirt extending from the plate toward the ground surface.

12. The portable disinfection apparatus of claim 9 further comprising a scanner that reads an encoded object when the portable disinfection apparatus is in a correct position for disinfection of the area.

13. The portable disinfection apparatus of claim 12 wherein the scanner is mounted on the enclosure.

14. The portable disinfection apparatus of claim 12 wherein the scanner is an optical scanner, and the encoded object is an image on the ground surface.

* * * * *